United States Patent [19]

Nowak

[11] Patent Number: 5,026,719
[45] Date of Patent: Jun. 25, 1991

[54] MICROBICIDAL AGROCHEMICAL COMPOSITIONS

[75] Inventor: Edward Nowak, Histon, England

[73] Assignee: Ciba-Geigy Corporation, Ardsley, N.Y.

[21] Appl. No.: 56,827

[22] Filed: Jun. 1, 1987

[30] Foreign Application Priority Data

Jun. 7, 1986 [GB] United Kingdom ................. 8613913

[51] Int. Cl.$^5$ ............................................ A01N 43/64
[52] U.S. Cl. ................... 514/383; 514/231.2
[58] Field of Search ............................. 514/231.2, 383

[56] References Cited

U.S. PATENT DOCUMENTS 2,687,397  9/1951  Dannenberg ..................... 525/513
3,642,995  2/1972  Schenk et al. .................... 424/248

FOREIGN PATENT DOCUMENTS 0074329  3/1983  European Pat. Off. .
1187633  4/1970  United Kingdom ............ 514/231.2
1522657  8/1978  United Kingdom .

OTHER PUBLICATIONS

Ernst-Heinrich Pommer, Pestic. Sci., 15, pp. 285-295 (1984).

Primary Examiner—Stanley J. Friedman
Assistant Examiner—Kevin Weddington
Attorney, Agent, or Firm—George R. Dohmann; Edward McC. Roberts

[57] ABSTRACT

New microbicidal compositions having improved microbicidal activity comprise a compound of formula I:

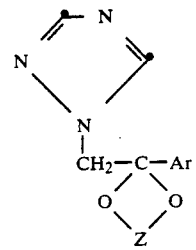

or an acid addition salt thereof; in which Z is $-CH_2CH_2-$, $-CH_2CH_2CH_2-$, $-CH(CH_3)-CH(CH_3)-$ or $-CH_2-CH(C_1-C_{10}alkyl)-$; and Ar is a phenyl, thienyl, halothienyl or naphthyl group, or phenyl substituted with 1 to 3 halogen, $C_1-C_4$alkyl, $C_1-C_4$alkoxy, cyano or nitro substituents; and a compound having the formula II:

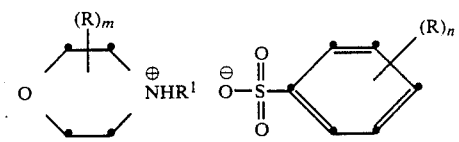

in which R is $C_1-C_4$alkyl, $R^1$ is hydrogen or $C_1-C_4$-alkyl, m is 0, 1, 2, 3 or 4 and n is 0, 1, 2, 3 or 4; new salts of (restricted) formula II, a process for their preparation and a method for combatting microbicidal plant diseases using the above mentioned compositions.

7 Claims, No Drawings

MICROBICIDAL AGROCHEMICAL COMPOSITIONS

The present invention relates to morpholine alkyl aryl sulphonates; their manufacture; and their use in fungicidal compositions for controlling harmful microorganisms, especially phytopathogenic fungi.

In British patent specification No. 1522657, there are described microbicidal compositions comprising, as active ingredient, a compound having the formula I:

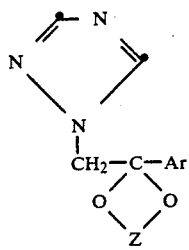

or an acid addition salt thereof; in which Z is —CH$_2$CH$_2$—, —CH$_2$CH$_2$CH$_2$—, —CH(CH$_3$)—CH(CH$_3$)— or —CH$_2$—CH(C$_1$-C$_{10}$alkyl)—; and Ar is a phenyl, thienyl, halothienyl or naphthyl group, or phenyl substituted with 1 to 3 halogen, C$_1$-C$_4$alkyl, C$_1$-C$_4$alkoxy, cyano or nitro substituents.

These compounds have found great commercial success when formulated as sole fungicidally-active ingredients in fungicidal compositions for use in agriculture, or in combination with other known fungicides such as tridemorph or carbendazim.

The compounds of formula I whether used alone, or in combination with other fungicides, are conventionally formulated as emulsifiable concentrates using organic solvents. They can be formulated however, with a hydrotrope viz. a water-soluble compound which tends to increase the solubility of other materials in aqueous solution, e.g. in the manner described in European Patent Application No. 74329. Hydrotopes are water soluble compounds which are capable to enhance the water solubility of a second in water only poorly soluble compound (Chemiker Zeitung; 95 (1971) 507–511). Further the use of hydrotropic substances is known for the preparation of microemulsions (FR-A 2187227, FR-A 2187226).

Hydrotropes are inter alia the alkali metal- or ammonium salts of lower alkylbenzene sulfonic acids e.g. sodium toluene sulfonate, sodium xylene sulfonate and ammonium cumene sulfonate. Such hydrotropes known from the state of the art do not enhance the fungicidal activity of fungicidal formulations containing them.

We have now found, surprisingly, that the use of a specific type of hydrotrope in conjunction with a compound of formula I, provides a formulation which exhibits enhanced microbicidal activity when compared to the conventional hydrotrope formulations.

Accordingly, the present invention provides a microbicidal composition comprising a compound of formula I; and a compound having the formula II:

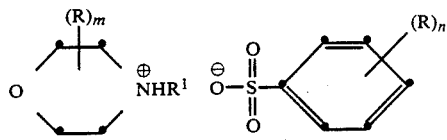

in which R is selected from the group consisting of C$_1$-C$_4$alkyl, R$_1$ is hydrogen or C$_1$-C$_4$alkyl, m is 0, 1, 2, 3 or 4 and n is 0, 1, 2, 3 or 4.

Compounds of formula I preferred for use in the compositions of the present invention include:
1-[2-(2,4-dichlorophenyl)-1,3-dioxolan-2-ylmethyl]-1H-1,2,4-triazole;
1-[2-(2,4-dichlorophenyl)-4-methyl-1,3-dioxolan-2-ylmethyl]-1H-1,2,4-triazole;
1-[2-(2,4-dichlorophenyl)-4-ethyl-1,3-dioxolan-2-ylmethyl]-1H-1,2,4-triazole;
1-[2-(2,4-dichlorophenyl)-4-propyl-1,3-dioxolan-2-ylmethyl]-1H-1,2,4-triazole (propiconazole); and
1-[2-(2,4-dichlorophenyl)-4-pentyl-1,3-dioxolan-2-ylmethyl]-1H-1,2,4-triazole;
or the agrochemically-compatible acid addition salts thereof e.g. those formed with inorganic acids such as a hydrohalic acid, sulfonic acid, nitric acid or phosphoric acid or an organic acid such as acetic acid, propionic acid or malonic acid.

Propiconazole is the preferred compound of formula I.

The production of the compounds of formula I is described in British patent specification No. 1522657.

Compounds of formula II which are preferred for use in the compositions of the invention are:
morpholine benzene sulfonate,
morpholine toluene sulfonate,
morpholine cumene sulfonate,
N-methylmorpholine benzene sulfonate,
N-methylmorpholine cumene sulfonate,
2-methylmorpholine benzene sulfonate,
2-methylmorpholine toluene sulfonate,
2-methylmorpholine xylene sulfonate,
2,6-dimethylmorpholine benzene sulfonate,
2,6-dimethylmorpholine xylene sulfonate,
2,2,6-trimethylmorpholine cumene sulfonate,
2,2,6,6-tetramethylmorpholine cumene sulfonate,
in particular morpholine cumene sulfonate, N-methylmorpholine cumene sulfonate and 2,6-dimethylmorpholine cumene sulfonate.

The compounds of formula II are new. Only morpholine benzene sulfonate and morpholine 4-toluene sulfonate have already been described in scientific literature (Beilstein, Handbuch d. Org. Chem.; Vol. 27 IV, 21). Those compounds of formula II which are not state of the art are new and a further object of this invention.

Accordingly, the present invention also provides new compounds having the formula II:

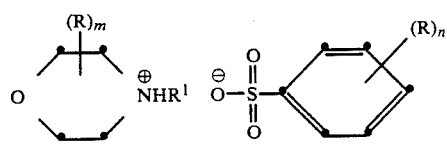

in which
R is selected from the group consisting of C$_1$-C$_4$-alkyl $R^1$ is hydrogen or $C_1$-$C_4$-alkyl
m is 0, 1, 2, 3 or 4 and
n is 0, 1, 2, 3 or 4 with the proviso that $R^1$ is not hydrogen if m and n are 0 or if m is 0 and $(R)_n$ stands for a 4-methyl group.

Preferred compounds of formula II include:
morpholine cumene sulfonate
N-methylmorpholine benzene sulfonate
N-methylmorpholine cumene sulfonate,
2-methylmorpholine benzene sulfonate,
2-methylmorpholine toluene sulfonate,
2-methylmorpholine cumene sulfonate,
2,6-dimethylmorpholine benzene sulfonate,
2,6-dimethylmorpholine cumene sulfonate,
2,2,6-trimethylmorpholine cumene sulfonate and
2,2,6,6-tetramethylmorpholine cumene sulfonate;
especially preferred are the morpholine cumene sulfonates of formula II, in which m=0, 1, 2, 3 or 4, R is methyl or ethyl and $R^1$ is methyl or ethyl; most preferred are N-methylmorpholine cumene sulfonate and 2,6-dimethylmorpholine cumene sulfonate.

The salts of formula II may be prepared by reacting an optionally substituted morpholine compound having the formula III:

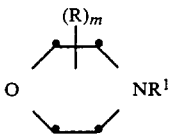
III in which R, $R^1$, m and n have their previous significance, with an optionally substituted benzene sulfonic acid of formula IV:

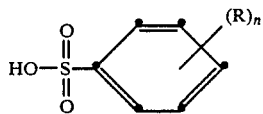
IV in which R and n have their previous significance; and then isolating the salt of formula II so formed, e.g. in solid form or as solution.

The reaction is conveniently effected by reacting substantially stoichiometric amounts of the compounds of formula III and IV, respectively, at a temperature ranging from ambient up to 100° C. Optionally a reaction solvent e.g. water, ethyl acetate, isopropyl alcohol or ethyl alcohol may be used. The most suitable solvent in above mentioned reaction is most preferably selected in view of the fact whether one wants to obtain the compound of formula II in solution or in crystalline form. If the isolation in crystalline form is intended it is preferred to perform the reaction of III with IV in a solvent in which the educts III and IV are soluble but the salt II formed is insoluble or only sparingly soluble. The salt of formula II can be used as hydrotopes in a very preferred manner for the production of aqueous concentrates of compounds of formula I as it will be stated later on. In this case it is preferred to accomplish the reaction of the educts III and IV in water; the aqueous solution of salt II thus formed can be used for the hydrotope formulation without any further purification.

The compositions of the present invention have an improved microbicidal spectrum against phytopathogenic fungi and bacteria especially *Erysiphe graminis* (powdery mildew). They also have very advantageous curative, systemic and, in particular, preventive properties, and can be used for protecting numerous cultivated plants. With the compositions of the invention it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compositions of the invention are effective against the phytopathogenic fungi belonging to the following classes: Fungi imperfecti (e.g. Botrytis, Helminthosporium, Fusarium, Septoria, Cercospora and Alternaria); Basidiomycetes (e.g. of the genera Hemileia, Rhizocotonia, Puccinia); and, in particular, against the class of the Ascomycetes (e.g. Venturia, Podosphaera, Erysiphe, Monilina, Uncinula). In addition, they can also be used as seed dressing agents for protecting seeds (fruit, tubers, grains) and plant cuttings against fungus infections as well as against phytopathogenic microorganisms which occur in the soil.

The invention further embraces the preparation of agrochemical compositions which comprises homogeneously mixing the active ingredients of formula I and II with one or more compounds or groups of compounds described herein. The invention furthermore relates to a method of treating plants, which comprises applying thereto or to their environment the composition of the present invention.

Target crops to be protected within the scope of the present invention comprise e.g. the following species of plants: cereals (wheat, barley, rye, oats, rice, sorghum and related crops), beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sun-flowers, coconuts, castor oil plants, cocoa beans, groundnuts), cucumber plants (cucumber, marrows, melons), fibre plants (cotton, flax, hamp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites), but especially cereals in particular wheat (winter and spring varieties) and barley (winter and spring varieties).

Compositions of the invention can be applied to the crop area or plant to be treated, simultaneously or in succession, with further agrochemically useful compounds. These compounds can be both fertilisers or micronutrient donors or other preparations that influence plant growth. They can also be selective herbicides, further fungicides in particular tridemorph, fenpropimorph and/or carbendazim, bactericides, nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying an agrochemical composition of the invention is foliar application. The number of applications and the rate of application depend on the risk of infestation by the corresponding pathogen (type of fungus). However, the composition of the invention can also penetrate the plant through the roots via the soil (systemic action) by impregnating the locus of the plant with a liquid composition. The compositions of the invention may also be applied to seeds (coating) by impregnating the seeds or other propagating material (such as shoots and lumps) with a liquid formulation of a composition of the invention. The coated propagating material thus obtained is a further object of this invention. In special cases, further types of application are also possible, e.g. selective treatment of the plant stems or buds.

The compositions of the invention are formulated in known manner to emulsifiable concentrates, coatable pastes, directly sprayable or dilutable solutions, dilute emulsions, suspension concentrates, wettable powders or water dispersible granules. As with the nature of the compositions, the methods of application, such as dipping, wetting, spraying or atomising, are chosen in accordance with the intended objectives and the prevailing circumstances.

Advantageous rates of application are normally from 50 g to 5 kg of active ingredient (a.i.) per hectare, preferably from 100 g to 2 kg a.i./ha, most preferably from 200 g to 600 g a.i./ha.

The compositions of the invention are prepared in known manner, e.g. by homogeneously mixing and/or grinding the active ingredients with extenders, e.g. solvents, and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ethers, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The surfactants customarily employed in the art of formulation are described e.g. in "1985 International Mc. Cutcheon's Emulsifiers and Detergents" Glen Rock, NY 07452, USA; "Encyclopedia of Surface Active Agents", Chemical Publishing Co., Inc. New York, 1980.

Suitable surface-active compounds are nonionic, ampohoteric and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Preferred surfactants for use in the compositions of the invention are non-ionic surfactants. Non-ionic surfactants are preferably polyglycol ether and -ester derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

The microbicidal compositions according to the invention contain as active substances a triazole of formula I together with a synergistically active amount of a compound of formula II. They usually contain 0.1 to 99% preferably 0.1 to 95%, of a compound of the formula I, 99.9 to 1%, preferably 99.8 to 5%, of a compound of formula II, 0 to 25% of a surfactant, and 0 to 25% of a solvent.

Whereas commercial products are preferably formulated as concentrates, the end user will normally employ dilute formulations. In a very advantageous manner the microbicidal compositions according to this invention can be formulated as aqueous solvent concentrates in accordance to the hydrotope formulations as described in EP-A No. 74329 to which is referred to. Whereas the salts of formula II are considered as hydrotopic active substances, the triazoles of formula I are the essentially water insoluble compounds which are dissolved in an aqueous solution of salts of formula II. The hydrotopic activity of salts of formula II can be used in a very advantageous manner for the preparation of aqueous concentrates with up to 75% by weight (vol) of compounds of formula I in aqueous solution of upto 70% by weight (vol) of hydrotopes of formula II. Most preferred are concentrates obtained by dissolving 5 to 50% by weight (vol) of a compound of formula I in a 5 to 70% by weight (vol) aqueous solution of formula II.

The following Examples further illustrates the present invention.

EXAMPLE 1

20 parts by weight of cumene sulphonic acid, as Eltesol CA96 (ex Albright and Wilson), are added to an equal weight of ethyl alcohol. The stirred solution is cooled to 20° C. and 8.7 parts by weight of morpholine are added, the temperature being maintained below 35° C.

The solution is stirred for a further 15 mins. after the addition is complete, then cooled to −5° C. and allowed to crystallise. After 24 hours, this solid is filtered, washed three times with cold diethyl ether and dried in a desiccator over silica gel. Melting point of dried material, morpholine cumene sulfonate is 101°–105° C.

EXAMPLE 2

20 parts by weight of cumene sulphonic acid, as Eltesol CA96, (ex Albright and Wilson), are added to an equal weight of deionised water. The stirred solution is cooled to 20° C. and 11.6 parts by weight of 2,6-dimethyl morpholine, as the 99% pure material, are added, dropwise, the temperature being maintained below 35° C.

Once the addition is complete the solution is diluted with further deionised water to produce an aqueous 60% w/w solution of 2,6-dimethyl morpholine cumene sulfonate (DMMCS).

EXAMPLE 3

Propiconazole 125EC (Emulsifiable Concentrate)

| | g/l |
|---|---|
| Propiconazole | 125 |
| 2,6-Dimethyl morpholine cumene sulfonate | 580 |
| Water | approx 390 |

The 2,6-dimethyl morpholine cumene sulfonate (DMMCS) is dissolved in the water, the propiconazole is added and the whole is stirred until a homogeneous solution is obtained.

EXAMPLE 4

Propiconazole 250EC

| | g/l |
|---|---|
| Propiconazole | 250 |
| Cyclohexanone | 100 |
| $C_{10}$alcohol ethoxylate (Ethylan CD 913, Lankro Chemical Ltd., Manchester) | 30 |
| Ethylene oxide/propylene oxide block co-polymer (Pluronic F 108, BASF Wyandotte Corp., USA) | 15 |
| Morpholine cumene sulfonate | 420 |
| Water | approx. 270 |

The morpholine cumene sulfonate is dissolved in water, followed by the alcohol ethoxylate and EO/PO block co-polymer. The cyclohexanone and propiconazole are then added and the whole is agitated until an homogeneous solution is obtained.

EXAMPLE 5

Propiconazole +Carbendazim 225SC (Suspension Concentrate)

| | g/l |
|---|---|
| Propiconazole | 125 |
| Carbendazim | 100 |
| Ethoxylated polyarylphenol/phosphate (Soprophor FL, ex Rhone Poulenc) | 60 |
| Silicone antifoam emulsion (Foammaster UDB) | 5 |
| Fumed silica (Aerosil COK-84, ex Degussa) | 10 |
| DMMCS | 470 |
| Water | approx. 330 |

The DMMCS is dissolved in water followed by the ethoxylated polyaryl phenol phosphate and propiconazole. Using a magnetic stirrer, the silicone antifoam, carbendazine and fumed silica are dispersed into the solution. The suspension is then wet-milled to produce a fine suspension with an average particle size of less than 2 microns.

EXAMPLES 6 AND 7

To highlight the improvement in mildew control when using compositions of the present invention, a 5 replicate test is performed in a glass house.

Spring Barley (Golden Promise) seedlings grown in trays in a glass house are infected with *Erysiphe graminis* (powdery mildew). The plants are left in the glass house until leaf infection reaches 10% of surface area.

At this point the seedlings are sprayed with aqueous dispersion consisting of propiconazole or propiconazole and carbendazim. Alongside are sprayed identical dispersions containing the two active ingredients in combination with morpholine aryl sulfonates, and also the morpholine aryl sulfonates alone.

The extent of mildew control, crop vigour and green leaf area is assessed after 7, 14 and 21 days. The results are summarised in Table 1.

| | | | 7 days | | | 14 days | | | 21 days | | |
|---|---|---|---|---|---|---|---|---|---|---|---|
| Example | Treatment | g/ha | mildew[Y] | crop* vigour | green leaf area | mildew[Y] | crop* vigour | green leaf area | mildew[Y] | crop* vigour | green leaf area |
| — | Untreated | — | 25.4 | 1.8 | — | 88.0 | 7.6 | 14.6 | 92.6 | 8.6 | 8.2 |
| — | 2,6-Dimethyl morpholine cumen sulfonate (DMMCS) | 480 | 29.4 | 2.4 | — | 86.4 | 7.8 | 15.5 | 96.0 | 8.5 | 4.6 |
| — | Morpholine cumene sulfonate (MCS) | 480 | 32.6 | 2.2 | — | 89.0 | 7.9 | 12.0 | 97.6 | 8.9 | 3.4 |
| — | Propiconazole | 125 | 17.2 | 1.4 | — | 32.6 | 3.6 | 72.4 | 71.6 | 6.0 | 33.4 |
| 6 | Propiconazole + DMMCS | 125 +480 | 14.8 | 1.8 | — | 14.8 | 2.6 | 83.0 | 35.4 | 4.2 | 68.0 |
| — | Pripiconazole + Carbendazim | 125 +100 | 14.6 | 1.8 | — | 27.2 | 3.4 | 72.6 | 51.0 | 5.6 | 45.0 |
| 7 | Propiconazole + Carbendazim + DMMCS | 125 +100 +480 | 16.6 | 2.0 + | — | 19.2 | 2.6 | 83.6 | 28.0 | 4.3 | 71.0 |

*Crop vigour is assessed on a 1-9 scale.
1 = no visible damage.
9 = total crop kill.
Y Expressed as a percentage of the leaf area infected.

EXAMPLES 8 TO 11

Using replicated field trials, the control of mildew on Spring Barley (Golden Promise) was assessed using different microbicidal compositions. 27 days after the first application the application of the active substance was repeated. The tests were evaluated 27 days after the first and 10 days after the second (37 days after the first) application. The results are summarised in Table 2.

| Example | Treatment | g/ha | 27 days after first application mildew | 37 days after first application mildew | yield (tonnes/ hectare) |
|---|---|---|---|---|---|
| — | Untreated | | 22.4 | 74.0 | 4.88 |
| — | propiconazole | 125 | 5.5 | 27.6 | 5.19 |

-continued

| Example | Treatment | g/ha | 27 days after first application mildew | 37 days after first application mildew | yield (tonnes/ hectare) |
|---|---|---|---|---|---|
| — | propiconazole carbendazim | 125 100 | 8.76 | 36.8 | 5.31 |
| 8 | propiconazole MCS | 125 480 | 3.8 | 19.4 | 5.41 |
| 9 | propiconazole DMMCS | 125 480 | 3.7 | 23.2 | 5.26 |
| 10 | propiconazole carbendazim MCS | 125 100 480 | 7.90 | 29.0 | 5.51 |
| 11 | propiconazole carbendazim DMMCS | 125 100 480 | 5.80 | 23.4 | 5.45 |

What is claimed is:

1. A microbicidal composition comprising a compound of formula I

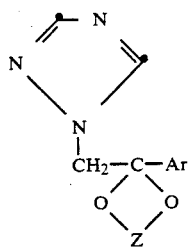

or an acid addition salt thereof; in which Z is —CH$_2$CH$_2$—, —CH$_2$CH$_2$CH$_2$— —CH(CH$_3$)—CH(CH$_3$)—or —CH$_2$—CH(C$_1$-C$_{10}$alkyl)-; and Ar is a phenyl, thienyl, halothienyl or naphthyl group, or phenyl substituted with 1 to 3 halogen, C$_1$-C$_4$alkyl, C$_1$-C$_4$alkoxy, cyano or nitro substituents together with a synergistically active amount of a compound of formula II

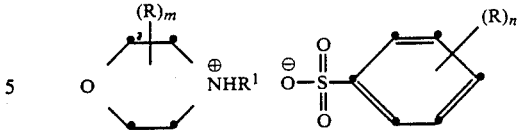

in which R is selected from the group consisting of C$_1$-C$_4$alkyl, R$_1$ is hydrogen or C$_1$-C$_4$alkyl, m is 0, 1, 2, 3 or 4 and n is 0, 1, 2, 3 or 4.

2. A microbicidal composition according to claim 1, wherein the compound of formula I is
1-[2-(2,4-dichlorophenyl)-1,3-dioxolan-2-ylmethyl]-1H-1,2,4-triazole;
1-[2-(2,4-dichlorophenyl)-4-methyl-1,3-dioxolan-2-ylmethyl]-1H-1,2,4-triazole;
1-[2-(2,4-dichlorophenyl)-4-ethyl-1,3-dioxolan-2-ylmethyl]-1H-1,2,4-triazole;
1-[2-(2,4-dichlorophenyl)-4-propyl-1,3-dioxolan-2-ylmethyl]-1H-1,2,4-triazole (propiconazole); or
1-[2-(2,4-dichlorophenyl)-4-pentyl-1,3-dioxolan-2-ylmethyl]-1H-1,2,4-triazole.

3. A microbicidal composition according to claim 1, wherein the compound of formula II is
morpholine benzene sulfonate,
morpholine toluene sulfonate,
morpholine cumene sulfonate,
N-methylmorpholine benzene sulfonate,
N-methylmorpholine cumene sulfonate,
2-methylmorpholine benzene sulfonate,
2-methylmorpholine toluene sulfonate,
2-methylmorpholine xylene sulfonate,
2,6-dimethylmorpholine benzene sulfonate,
2,6-dimethylmorpholine xylene sulfonate,
2,2,6-trimethylmorpholine cumene sulfonate,
2,2,6,6-tetramethylmorpholine cumene sulfonate, in particular morpholine cumene sulfonate, N-methylmorpholine cumene sulfonate or
2,6-dimethylmorpholine cumene sulfonate.

4. A composition according to claim 1 containing 0.1 to 99% of a compound of formula I; 99.9% to 1% to a compound of formula II; 0 to 25% of a surfactant; and 0 to 25% of a solvent.

5. Aqueous concentrate according to claim 1 consisting up to 75% by weight (vol) of a compound of formula I dissolved in an up to 70% by weight (vol) aqueous solution of a salt of formula II.

6. A composition according to claim 1 containing propiconazole as compound of formula I.

7. A microbicidal composition comprising propiconazole together with a synergistic amount of a compound selected from a morpholine cumene sulfonate and 2,6-dimethylmorpholine cumene sulfonate.

* * * * *